US008176922B2

(12) United States Patent
Sherman et al.

(10) Patent No.: US 8,176,922 B2
(45) Date of Patent: May 15, 2012

(54) SYSTEM AND METHOD FOR BIDIRECTIONAL COMMUNICATION WITH AN IMPLANTABLE MEDICAL DEVICE USING AN IMPLANT COMPONENT AS AN ANTENNA

(75) Inventors: Jason T. Sherman, Warsaw, IN (US); Mark R. DiSilvestro, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 1931 days.

(21) Appl. No.: 10/880,003

(22) Filed: Jun. 29, 2004

(65) Prior Publication Data

US 2006/0009856 A1 Jan. 12, 2006

(51) Int. Cl.
*A61B 19/00* (2006.01)
(52) U.S. Cl. ........................................ 128/899
(58) Field of Classification Search .......... 128/897–899, 128/903; 607/60–62; 623/16.11, 17.11, 623/18.11, 19.11, 20.11, 20.14, 20.18, 20.21, 623/20.32, 20.34, 20.35, 22.11, 23.15
See application file for complete search history.

(56) References Cited

U.S. PATENT DOCUMENTS

| | | | |
|---|---|---|---|
| 5,193,539 A | 3/1993 | Schulman et al. |
| 5,197,488 A | 3/1993 | Kovacevic |
| 5,360,016 A | 11/1994 | Kovacevic |
| 5,425,775 A | 6/1995 | Kovacevic et al. |
| 5,469,862 A | 11/1995 | Kovacevic |
| 5,523,746 A | 6/1996 | Gallagher |
| 5,545,191 A | 8/1996 | Mann et al. |
| 5,626,630 A | 5/1997 | Markowitz et al. |
| 5,833,603 A | 11/1998 | Kovacs et al. |
| 5,861,019 A | 1/1999 | Sun et al. |
| 5,967,986 A | 10/1999 | Cimochowski et al. |
| 6,034,296 A | 3/2000 | Elvin et al. |
| 6,115,636 A | 9/2000 | Ryan |
| 6,169,925 B1 | 1/2001 | Villaseca et al. |
| 6,324,418 B1 | 11/2001 | Crowley et al. |

(Continued)

FOREIGN PATENT DOCUMENTS

EP 1172064 1/2002
(Continued)

OTHER PUBLICATIONS

National Semiconductor LM62 2.7V, 15.6 mVrC, SOT-23 Temperature Sensor, Jun. 1999 (7 pages) 2001 National! Semiconductor Corporation Article.

(Continued)

*Primary Examiner* — Charles A Marmor, II
*Assistant Examiner* — Christine D Hopkins
(74) *Attorney, Agent, or Firm* — Maginot, Moore & Beck

(57) ABSTRACT

A system and method enables data to be communicated from a position within a human body to an external data device. The system includes a wireless communication module that is electrically coupled to an implant component having a metal surface so that the implant component operates as an antenna in response to the application of a modulated carrier wave being applied to the implant component. The wireless communication module may be coupled to the implant component so that the implant component operates as a monopole or dipole antenna. When the monopole configuration is used, the system further includes a ground plane so that the electromagnetic field emitted by the implant component is reflected and the emitted and reflected fields resemble the emitted field of a dipole antenna for the carrier frequency.

28 Claims, 3 Drawing Sheets

U.S. PATENT DOCUMENTS

| | | | |
|---|---|---|---|
| 6,385,593 B2 | 5/2002 | Linberg | |
| 6,447,448 B1 | 9/2002 | Ishikawa et al. | |
| 6,456,256 B1 | 9/2002 | Amundson et al. | |
| 6,539,947 B2 | 4/2003 | Boies et al. | |
| 6,577,901 B2 | 6/2003 | Thompson | |
| 6,628,989 B1 | 9/2003 | Penner et al. | |
| 6,631,296 B1 | 10/2003 | Parramon et al. | |
| 6,656,117 B2 * | 12/2003 | Jentsch et al. | 600/300 |
| 6,706,005 B2 | 3/2004 | Roy et al. | |
| 6,708,065 B2 | 3/2004 | Von Arx et al. | |
| 6,802,811 B1 | 10/2004 | Slepian | |
| 7,047,076 B1 * | 5/2006 | Li et al. | 607/36 |
| 7,256,695 B2 * | 8/2007 | Hamel et al. | 340/572.1 |
| 2002/0013613 A1 | 1/2002 | Haller et al. | |
| 2002/0013614 A1 | 1/2002 | Thompson et al. | |
| 2002/0024450 A1 | 2/2002 | Townsend et al. | |
| 2002/0040234 A1 | 4/2002 | Linberg et al. | |
| 2002/0082665 A1 | 6/2002 | Haller et al. | |
| 2002/0091310 A1 | 7/2002 | Jentsch et al. | |
| 2002/0177782 A1 | 11/2002 | Penner | |
| 2002/0177884 A1 | 11/2002 | Ahn et al. | |
| 2002/0183806 A1 | 12/2002 | Abrahamson et al. | |
| 2003/0069644 A1 | 4/2003 | Kovacevic et al. | |
| 2003/0093503 A1 | 5/2003 | Yamaki et al. | |
| 2003/0172940 A1 | 9/2003 | Rogers et al. | |
| 2004/0010184 A1 | 1/2004 | Kenknight et al. | |
| 2004/0011366 A1 | 1/2004 | Schulman et al. | |
| 2004/0019382 A1 | 1/2004 | Amirouche et al. | |
| 2004/0049245 A1 | 3/2004 | Gass et al. | |
| 2004/0073279 A1 | 4/2004 | Malackowski et al. | |
| 2004/0078219 A1 | 4/2004 | Kaylor et al. | |
| 2004/0113790 A1 | 6/2004 | Hamel et al. | |
| 2004/0204744 A1 | 10/2004 | Penner et al. | |
| 2005/0010299 A1 | 1/2005 | Disilvestro | |
| 2005/0010301 A1 | 1/2005 | Disilvestro | |
| 2005/0010302 A1 | 1/2005 | Dietz et al. | |
| 2005/0061336 A1 | 3/2005 | Goetz et al. | |

FOREIGN PATENT DOCUMENTS

| | | |
|---|---|---|
| EP | 1264514 | 12/2002 |
| EP | 1264614 | 12/2002 |
| WO | 9217113 | 10/1992 |
| WO | 00/13585 A1 | 3/2000 |
| WO | WO 00/13585 | 3/2000 |
| WO | 0119239 | 3/2001 |
| WO | 0143823 | 6/2001 |
| WO | 0148675 | 7/2001 |
| WO | 03066159 | 8/2003 |
| WO | 03077752 | 9/2003 |
| WO | 03095024 | 11/2003 |
| WO | 2004028627 | 4/2004 |
| WO | 2004030757 | 4/2004 |
| WO | 2004030759 | 4/2004 |
| WO | 2004/039256 A2 | 5/2004 |
| WO | WO 2004/039256 | 5/2004 |

OTHER PUBLICATIONS

"Surgeon at Scripps Clinic Implants One-of-a-Kind 'Electronic Knee'—Revolutionizing Research in Knee Implant Technology" (3 pages) Scripps Clinic Oct. 21, 2004 Article.

European Search Report for EP Application No. 05257763.2-2305, Mar. 13, 2006, 2 pages.

"Application Note" nRF24E1 and nRF24E2 RF layout nAN24-03 Jun. 2004 (6 pages) Nordic Semiconductor ASA (Revision 2.0).

European Search Report for European Application No. EP05257906.7-2305, Mar. 30, 2006, 6 pages.

European Search Report for European Application No. EP05257906.7-2305, Mar. 30 , 2006, 6 pages.

* cited by examiner

SYSTEM AND METHOD FOR BIDIRECTIONAL COMMUNICATION WITH AN IMPLANTABLE MEDICAL DEVICE USING AN IMPLANT COMPONENT AS AN ANTENNA

FIELD OF THE INVENTION

This invention relates to joint implant systems and, more particularly, to joint implant systems that communicate with other medical data devices.

BACKGROUND OF THE INVENTION

Joints in the body are comprised of bones with articulating surfaces that move against or in close proximity with one another in the joint. For example, the knee is a joint that includes the distal end of the femur that terminates into the medial and lateral condyles, which cooperate with both the patella and the meniscus of the proximal tibia for joint movement. Bone disease, such as arthritis, may deteriorate one or more joint compartments so that movement in the joint produces pain. One remedy for joints deteriorated by disease or injury is replacement of one or more compartments of the joint with artificial implants. For example, a total knee replacement (TKR) may be performed by surgically opening the knee, removing the diseased portions of the distal femur, proximal tibia, and/or patellar surface, and implanting an artificial prosthesis. The biocompatible materials used to make the bone prosthesis reduce the risk of infection and wear well.

One important aspect of using artificial implants to repair a diseased joint is the fit of the artificial implants with one another and the patient's joint physiology. That is, implant size, shape, and location are important parameters for enabling patient movement that complies with the ligaments and muscles of the patient. During the recovery and rehabilitation period following a surgery, information regarding the placement and stability of the implant components is useful to determine whether the surgery went as planned and whether healing is occurring as expected.

Data regarding the implant components and their integration into the patient's joint may be obtained using radiographic images, magnetic resonance imaging, and computerized tomography scans. These methods produce images of the joint at particular points in time in the rehabilitation period, but they suffer from a number of shortcomings. For one, some of these techniques require the joint to be immobilized, otherwise image quality is compromised. For another, images typically cannot be generated of the joint while the patient is performing exercises or other rehabilitation activities. Additionally, images developed by these techniques are not real-time nor do they provide measurements of forces active in the joint. Continuous and accurate information regarding the implant components during rehabilitation sessions would have significant value in the evaluation of a joint replacement surgery.

In an effort to provide parameter measurements in the vicinity of orthopaedic components implanted in a patient, sensors and telemetry modules, which transmit the parameters measured by the sensors, have been coupled with bone fixation devices and bone fusing implants. For example, U.S. Pat. No. 6,034,296 discloses a bone fixation device to which a strain sensor and a telemetry unit are mounted. The strain sensor generates a signal that corresponds to the magnitude of the strain being sensed by a bone fixation device being used to repair a fracture. The signal is provided by a conductor to the telemetry unit so the signal may be used to modulate a signal transmitted over an antenna that is coupled to the telemetry unit. In U.S. Pat. No. 6,706,005, a sensor and a telemetry module are associated with a ventral cervical stabilization system to provide data regarding a bone fusion on a patient's spinal column. Again, data derived from one or more sensors coupled to the telemetry unit are wirelessly communicated to a device external to the patient by modulating a signal from the telemetry unit with the data and radiating the resulting signal through an antenna. Wireless communication is preferred because wires extending through the skin of the patient present opportunities for infections.

In these previously known wireless communication systems that may be implanted in a patient, the antenna is a component of the telemetry module that must be micro-machined or micro-fabricated for wireless communication with a communication unit that is external to the patient's body. The antenna may be incorporated in the telemetry module or sensor. Alternatively, the antenna may be manufactured as a separate component in the system and coupled to the telemetry unit. Consequently, the antenna design and manufacture further complicates the inclusion of the parameter sensor and electronics module with a bone fixation device or orthopaedic component.

What is needed is a way of providing continuous and real-time data from a joint in which a complete or partial joint replacement surgery has occurred without requiring antenna micro-machining or micro-fabrication in the telemetry unit.

What is needed is a way of providing continuous and real-time data from a joint in which a complete or partial joint replacement surgery has occurred without requiring the manufacture of a separate antenna component for the system.

SUMMARY OF THE INVENTION

The above limitations of previously known systems for wirelessly communicating data from a sensor or data module located within a patient have been overcome by a system and method operating in accordance with the principles of the present invention. The inventive system includes an implant component having a metal surface and a wireless communication module electrically coupled to the implant component so that a length of the implant component operates as an antenna. Using the implant component as an antenna enables the wireless communication module to transmit data to an external device or receive data from the external device. The wireless communication module may be a module for sending a signal modulated with sensor data through the artificial implant or a module for receiving a data signal through the artificial implant. The wireless communication module may also be a transceiver for both transmitting and receiving signals through the implant component.

In the system of the present invention, the wireless communication module may be coupled to the implant component at a point where the length of the implant component that operates as an antenna is an integral number of half-wavelengths of the carrier wave for communication through the antenna. For example, the wireless communication module may be electrically coupled to the artificial implant approximately at its mid-point so the lengths of the artificial implant from the coupling point to each end are approximately as long as one quarter of the wavelength of the carrier wave. In this configuration, the artificial implant forms a dipole antenna for the wireless communication module.

The system of the present invention may also include a ground plane incorporated in an implant component so that the length of the implant component operating as an antenna may perform as a dipole antenna even though its length is not approximately one half of the wavelength of the carrier signal. The addition of a ground plane reflects the electromagnetic radiation emitted by the implant component coupled to the wireless communication module so the resulting field corresponds to that of a dipole antenna. This may be accomplished by coupling the wireless communication module to one end of an artificial implant having a length of approximately one quarter of the carrier signal wavelength to form a monopole antenna. The ground plane may be positioned so it reflects the emitted field and the total emitted and reflected field configuration resembles that of a dipole antenna. The ground plane may be incorporated in the implant component operating as an antenna or it may be incorporated in another implant component used to reconstruct the joint.

The wireless communication module may transmit or receive data on any of a number of frequencies that may be used for wireless communication in the environment of an operating room. For example, the wireless communication module may communicate on the Bluetooth frequency of 2.4 GHz. This frequency has a half wavelength of 5.945 centimeters in free space; however, the permittivity of body tissue differs from that of free space. In fact, different types of body tissue differ in permittivity. Thus, the implant or implant portion to be used as an antenna is selected or sized in accordance with the permittivity of the body tissue proximate the antenna and the frequency used for wireless communication with the antenna. The antenna may be sized to operate as a dipole or as a monopole antenna with a ground plane. The ground plane for a monopole antenna may be incorporated on another artificial implant component to generate a total emitted and reflected field corresponding to one generated by a dipole antenna that corresponds to the wireless frequency being used and the surrounding permittivity.

One advantage of the present invention is that an external communication device may be variably tuned until a response signal is received from an implant component. The frequency on which the response signal is received may be then be used to determine the half-wavelength of the signal and the length of the artificial implant through which the response signal is being transmitted. This information regarding implant length may be used to identify the system that was used to perform the partial or complete joint replacement surgery because different systems use components having different dimensions. This information is made available by the present invention without requiring the storage of identification data in the wireless communication module as required in some data communication systems that may be implanted in patients.

In one embodiment of the present invention, a tibial component for a knee replacement compartment has a wireless communication module coupled approximately to the mid-point of the tibial component. A pressure sensor is located proximate the tibial component to sense the pressure being applied to the tibia of the replacement knee. The sensor is coupled by a wire to the wireless communication module. The pressure signal generated by the pressure sensor is provided over the wire to the wireless communication module where it is used to modulate a carrier frequency having a half-wavelength equal to the length of the tibial component. An interrogation signal from an external data communication module activates the wireless communication module so that the modulated signal is coupled to the tibial component and radiated as a response signal to the external data communication device. The external communication device demodulates the response signal to obtain the pressure signal for data collection.

In another embodiment of the present invention, the tibial component is coupled to the wireless communication module so that the tibial component operates as a monopole antenna. Within the polyethylene bearing on which the condyles articulate, a ground plane is mounted so that the electromagnetic field emitted by the tibial component is reflected. Thus, the monopole antenna implemented by the tibial component generates a field that corresponds to that produced by a dipole antenna for the carrier frequency.

A method operating in accordance with the present invention includes electrically coupling a wireless communication module to an implant component having a metal surface and operating the implant component as an antenna for wireless communication between the wireless communication module and a data communication device external to a patient in which the implant component is implanted. The method includes transmitting a modulated carrier wave through the implant component operating as an antenna or receiving a modulated carrier wave through the implant component. The carrier wave transmitted through the implant component may be modulated with sensor data received from a sensor coupled to the wireless communication module. The modulated carrier wave received through the implant component may be demodulated by the wireless communication module to obtain a data signal from the external data communication device.

In the method of the present invention, the coupling of the wireless communication module to the implant component may occur at a point where the length of the implant component that operates as an antenna is an integral number of half-wavelengths of the carrier wave. For example, the coupling of the wireless communication module to the implant may occur at a point that enables the artificial implant component to operate as a dipole antenna for a corresponding frequency. This point may be located approximately at the mid-point of the implant component's length so the distance from the point of coupling to each end of the implant component is approximately one quarter of the wavelength of the carrier wave in body tissue.

The method of the present invention may also include incorporating a ground plane in an implant component so that the implant component operating as an antenna operates as a monopole antenna and the ground plane enables the implant component to generate a field that corresponds to one generated by a dipole antenna. The addition of a ground plane reflects the electromagnetic radiation emitted by the implant component operating as an antenna so the resulting field corresponds to that of a dipole antenna. This may be accomplished by coupling the wireless communication module to one end of an implant component having a length of approximately one quarter of the carrier signal wavelength in body tissue. The ground plane may be incorporated in the implant component operating as an antenna or another implant component used to reconstruct the joint. The ground plane is located in the joint so it reflects the electromagnetic field emitted by the implant component; hence the total emitted and reflected field configuration resembles that of a dipole antenna.

The wireless communication between the wireless communication module and the external data communication device may be carried on any of a number of frequencies for known wireless communication standards. For example, the wireless communication may be implemented using the Bluetooth frequency of 2.4 GHz. As noted above, the wavelength of this frequency may be used to define the coupling point for the implant component as a dipole or monopole antenna. The method of the present invention may also include variably tuning the external data communication device until a response signal is received from the wireless communication module. The frequency on which the response signal is received may be then be used to determine the half-wavelength of the signal and the length of the implant component through which the response signal is being transmitted. This information regarding implant length may be used to identify the system that was used to partially or completely reconstruct the joint.

The method of the present invention may include electrically coupling a wireless communication module to a tibial component for a knee replacement compartment for wireless communication with an external data communication device. A data signal generated by a sensor or memory module that is located proximate the tibial component is coupled by a wire to the wireless communication module. The data signal is used to modulate a carrier frequency that is radiated through the tibial component in response to an interrogation signal from the external data communication device. The external communication device demodulates the response signal to obtain the data signal for data collection.

The method of the present invention may also include coupling the tibial component to the wireless communication module so that the tibial component operates as a monopole antenna and providing a ground plane with a polyethylene bearing on which the condyles articulate so that the electromagnetic field emitted by the tibial component is reflected. Thus, the monopole antenna implemented by the tibial component generates a field that corresponds to that produced by a dipole antenna for the carrier frequency.

Thus, the system and method of the present invention enable wireless communication between a sensor and/or memory modules associated with a patient's replaced joint and an external data communication device without requiring separate fabrication of an antenna for the wireless communication.

The system and method of the present invention also enable the length of a component being operated as an antenna to be determined by variably tuning the external data communication device so the wireless communication module provides a response signal to the external device through the implant component.

The above described features and advantages, as well as others, will become more readily apparent to those of ordinary skill in the art by reference to the following detailed description and accompanying drawings.

DETAILED DESCRIPTION

Figure 1:
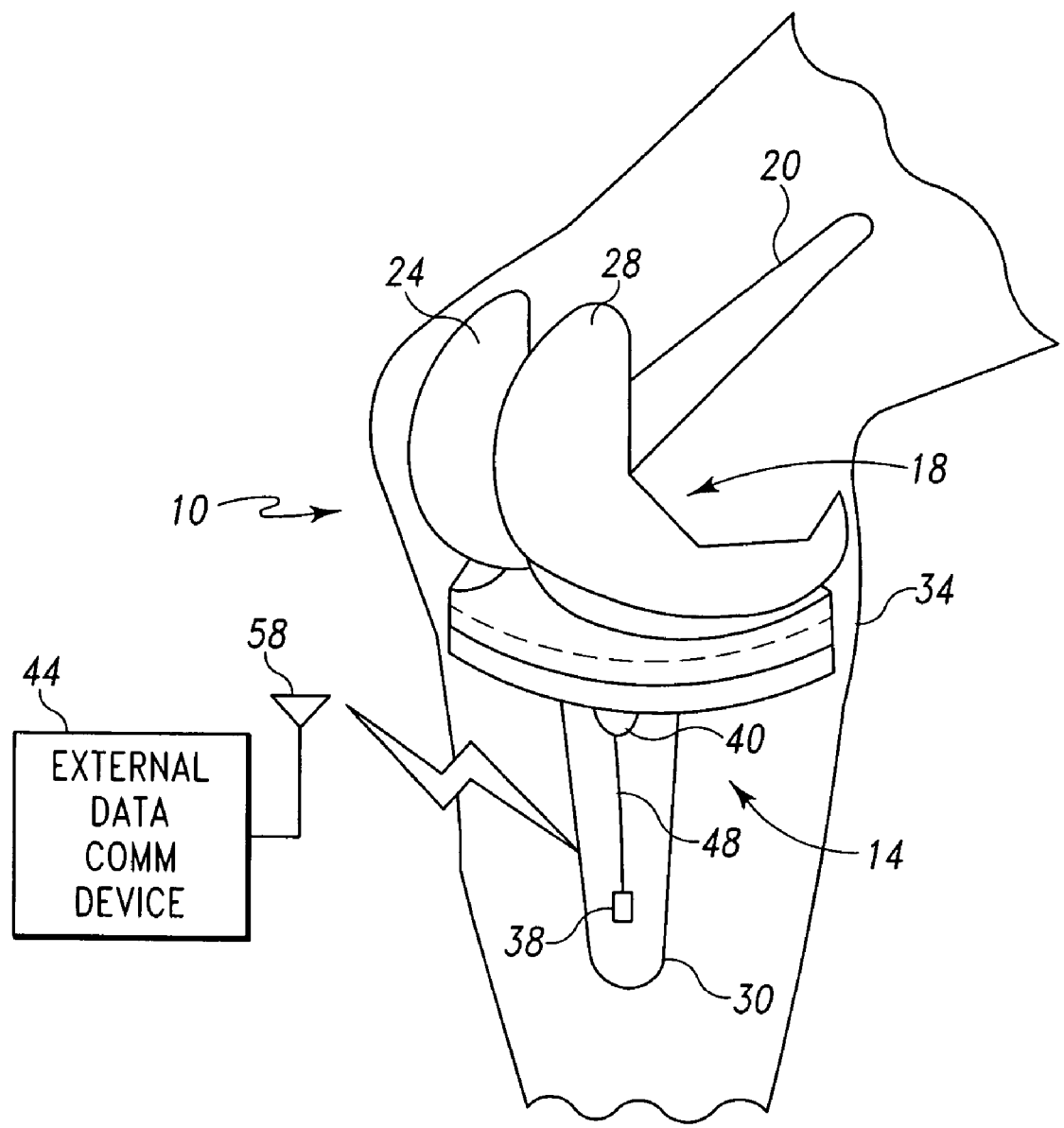
FIG. 1 is a depiction of a reconstructed knee in which a data communication system has been incorporated that uses an implant component as a dipole antenna.

Total joint replacement surgery typically involves resecting the bones that terminate at a joint and implanting prosthesis components that replace the portions of the bones that were removed so the articulation of the joint is improved. Total knee replacement (TKR) surgery may use a component system 10 having a tibial component 14 and a femoral component 18, such as the one that is shown in FIG. 1. The femoral component 18 includes a stem 20 having a lateral condyle 24 and a medial condyle 28 formed at one end, while the tibial component 14 includes a stem 30 having a bearing 34. Femoral component 18 may be installed in a patient's leg by first resecting the distal end of the femur so the stem 20 may be inserted into the remaining section of the femur and the condyles 24, 28 terminate the reconstructed femur. In TKR surgery, the proximal end of the tibia is also resected so that stem 30 may be inserted into the tibia so the lateral and medial condyles 24, 28 of the femoral component 18 may articulate on the bearing 34 of the tibial component 14. The components of a total or partial joint replacement system are typically constructed from a biocompatible metal, such as titanium.

In an embodiment of the present invention, a wireless communication module 38 and a sensor 40 may be mounted to tibial component 14 so that data from the reconstructed joint may be communicated with a device 44 external to the patient. Sensor 40 may also be a memory module that stores data that has been obtained in the vicinity of the reconstructed joint. Although the data communication system of the present invention is shown being implemented on the tibial component of a knee replacement system, it may also be implemented on other components of a knee replacement system. Additionally, data communication systems made in accordance with the principles of the present invention may be implemented on components in reconstruction systems for other joints and bones of the human body.

The wireless communication module 38 may be mounted to the outside of tibial component 14 and coupled via an electrical lead(s) 48 to one or more sensors mounted on the stem 30 of the tibial component 14. The wireless communication module 38 is also electrically coupled to the stem 30 of the tibial component 14. As explained more fully below, a signal from the wireless communication module 38 is radiated from the metal of the implant component to which the module 38 is electrically coupled for communication with the external device 44. In the embodiment of FIG. 1, the sensor 48 generates a signal corresponding to some measured parameter that is provided via the lead 48 to the wireless communication module 38 for communication through the tibial component 14 to the external device 44. The parameter measured by the sensor may be any parameter measured by known sensors and transducers, such as pressure, temperature, strain, or the like.

The sensor 48 may be a piezoresistive, piezoelectric, or capacitive type of sensor, but other types of sensors and transducers may be used as well. Piezoresistive, piezoelectric, and capacitive sensors are sensors having an electrical parameter that is altered by the force or parameter measured by the sensor. For example, piezoresistive sensors have an electrical resistance value that changes in response to the application of pressure on the sensor. A sensing current is provided through the sensor and changes in the resistance of the sensor are detected through changes in the current drawn through the sensor. The sensor 48 may also be a memory module that stores data regarding a reconstructed joint or tissue in the area of the reconstructed joint. The memory module provides the stored data to the wireless communication module 38 for communication with an external device.

A block diagram of one embodiment of the wireless communication module 38 that may be constructed in accordance with the principles of the present invention is shown in FIG.

2A. The wireless communication module 38 may include an RF-DC converter/modulator 50 and a control circuit 54. The RF-DC converter/modulator 50 converts the energy from a signal transmitted by the external device 44 that excites the portion of the tibial component 14 that operates as an antenna into a DC current for powering the control circuit 54 and the sensor 40. In response to the receipt of power from the external device 44, the sensor generates a signal that is delivered by the lead 48 to the control circuit 54. This signal is provided to the RF-DC converter/modulator 50 so it may be used to modulate a carrier wave generated by the converter/modulator 50. The modulated carrier wave is coupled to the tibial component 14 so it is radiated by the tibial component and received by the external communication device 44 through its antenna 58.

The RF-DC converter/modulator 50 of the wireless communication module 38 may be electrically coupled to the tibial component 14 by bond pads or by other known electrically conductive materials used electrical components implanted within the human body. The wireless communication module 38 may then be coated with a soft polymeric film, such as parylene, polydimethylsiloxane, or other biocompatible epoxy. The wireless communication module 38 may be implemented with an integrated circuit. More specifically, the wireless module 38 may be fabricated as an application specific integrated circuit (ASIC).

Figure 2A:
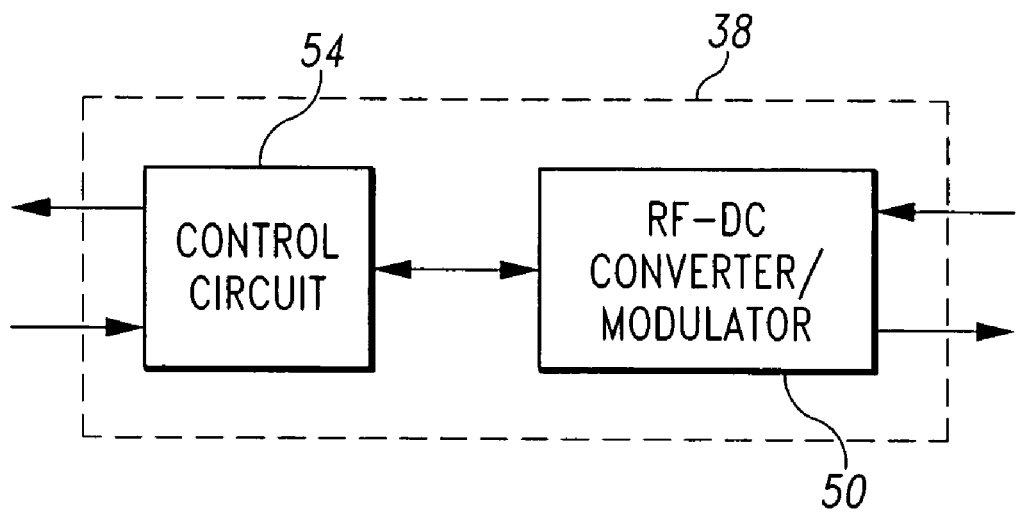
FIG. 2A is a block diagram of a wireless communication module that may be used in a data communication system incorporated in a reconstructed joint.
Figure 2B:
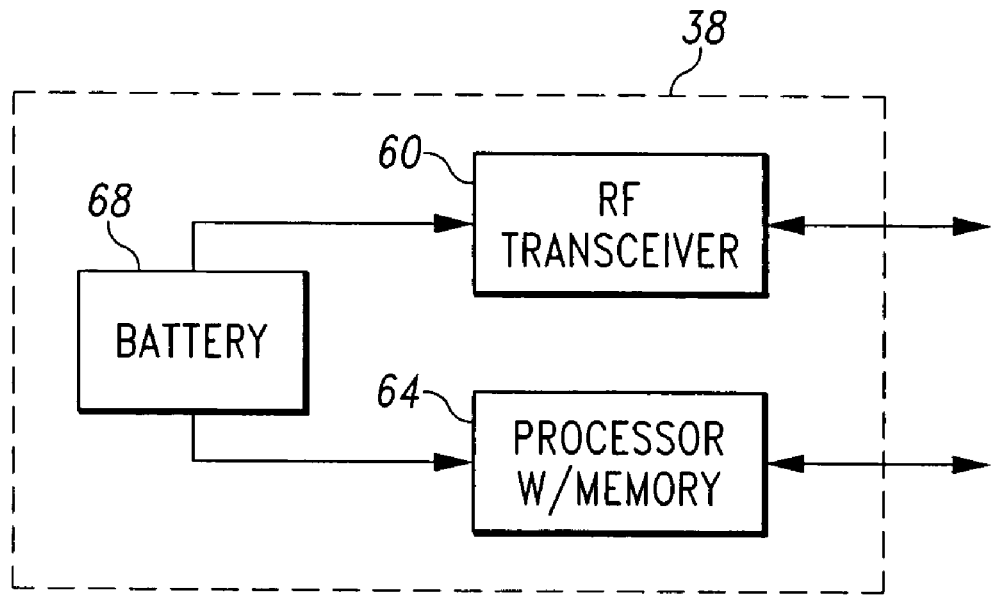
FIG. 2B is a block diagram of a wireless communication module that may be used in a data communication system incorporated in a reconstructed joint.

An alternative embodiment of the wireless communication module 38 that may be constructed in accordance with the principles of the present invention is shown in FIG. 2B. As depicted, the wireless communication module 38 may be comprised of an RF transceiver 60, a processor 64, and a battery 68. Battery 68 is provided to continuously supply power to the RF transceiver 60 and the processor 64. The processor 64 may be coupled through lead(s) 48 to one or more sensors 40 for measuring parameters in the vicinity of the joint in which the module 38 is implanted. The processor 64 may also be provided with memory so that signals from the sensor(s) 40 may be converted to a form that may be stored in the memory of the processor 64 for later retrieval by the external device 44. The memory may be internal to the processor or the memory may be a memory module external to the processor that is used for the storage of data. The RF transceiver is able to both transmit and receive signals through the implant component to which the wireless communication module is electrically coupled. In response to an interrogation signal or on some periodic basis, the processor 64 may retrieve data from its memory and provide the data to the RF transceiver 60. The RF transceiver 60 modulates a carrier wave with the data for transmission through the implant component to the external device 44. The RF transceiver 60 may also receive a signal from the external device 44 through the implant component and demodulate the signal to obtain data. These data may be provided to the processor 64 for immediate use or for storage in the processor, either for later use or for modification of the program controlling the operation of the processor 64.

The wireless communication module 38 may be electrically coupled to the tibial implant component, for example, at the midpoint of its length. In free space, this would mean that the RF-DC converter/modulator or RF transceiver would need to use a carrier wave having a frequency that corresponds to a signal with a wavelength that is twice as long as length of the tibial component. However, because the permittivity of body tissues is greater than free space, the frequency should be one having a wavelength that is as long as the length of the tibial component. For example, a signal having a half-wavelength in free space of 16 cm corresponds to 1 GHz, but in body tissue the half-wavelength would be 8 cm. Coupling the wireless communication module at the midpoint of an implant component that is 8 cm long would enable the implant module to act as a dipole antenna for a 1 GHz carrier wave.

The Bluetooth communication standard uses a carrier frequency of 2.4 GHz, which corresponds to a half-wavelength of 5.945 cm in free space. This frequency has a half-wavelength of 5.945 centimeters in free space; however, the permittivity of body tissue differs from that of free space. In fact, different types of body tissue differ in permittivity. Thus, the implant or implant portion to be used as an antenna is selected or sized in accordance with the permittivity of the body tissue proximate the antenna and the frequency used for wireless communication with the antenna. The antenna may be sized to operate as a dipole or as a monopole antenna with a ground plane. The ground plane for a monopole antenna may be incorporated on another artificial implant component to generate a total emitted and reflected field corresponding to one generated by a dipole antenna that corresponds to the wireless frequency being used and the surrounding permittivity. Thus, in the system of the present invention, the wireless communication module may be adapted to use a carrier frequency that conforms to the physical characteristics of the implant component being used as an antenna or the physical dimensions of the implant may be conformed to provide an antenna for a particular communication standard. In the present invention, it is contemplated that an implant component may be used as an antenna to communicate in accordance with the IEEE 802.11(a), 802.11(b), 802.11(g), 802.11(n), 802.15.1 (Bluetooth), 802.15.3 (WiMedia), 802.15.4 (ZigBee), 802.16 (Broadband Wireless Access), Wireless USB, Wavenis, and HomeRF standards, although other wireless communication standards may be used.

Figure 3:
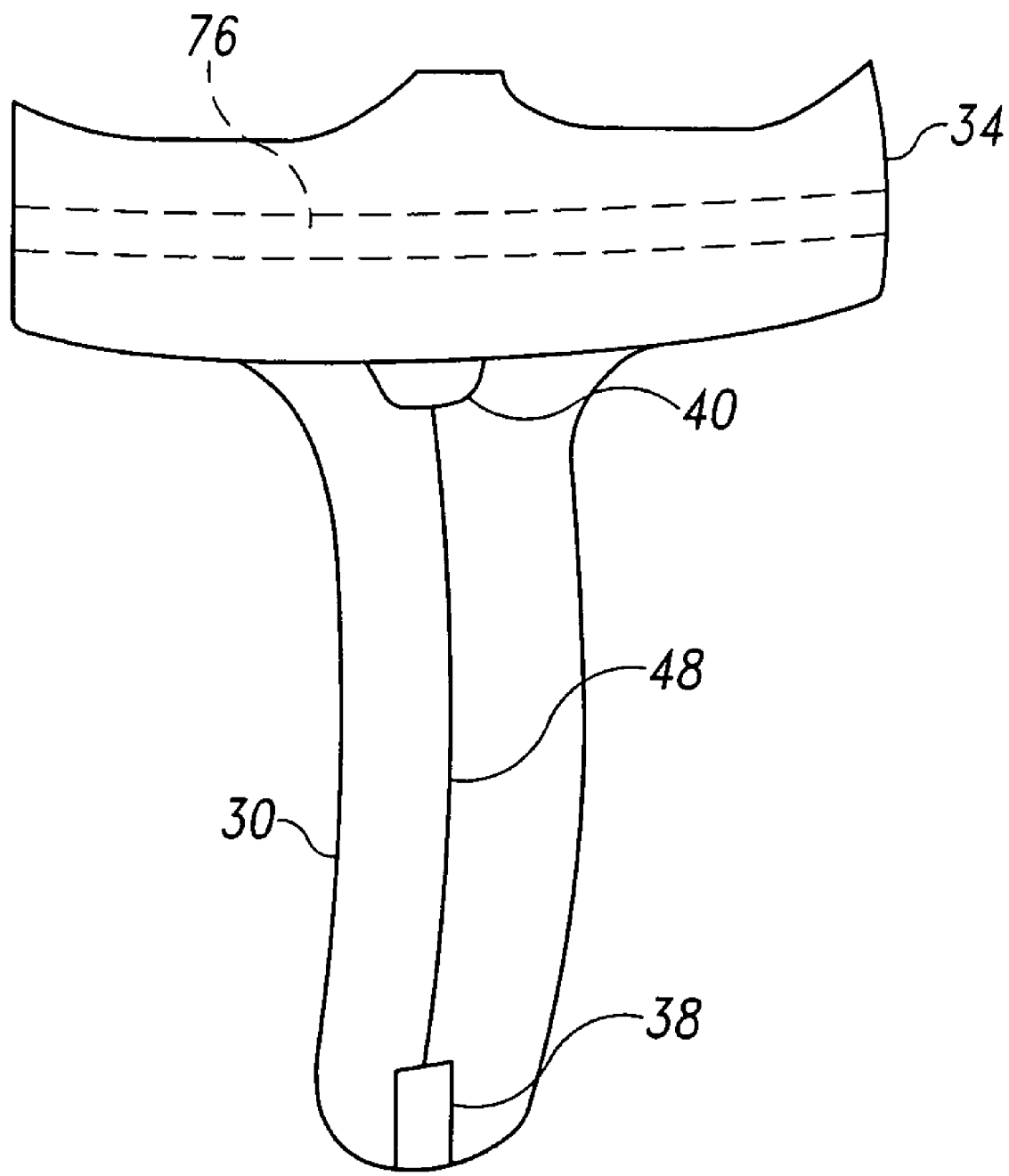
FIG. 3 is a depiction of a reconstructed knee in which a data communication system has been incorporated that uses an implant component as a monopole antenna.

To provide additional flexibility for configuring an implant component for operating as an antenna, a ground plane may be incorporated in an implant component so the implant operating as an antenna may be configured as a monopole antenna. For example, the tibial component of FIG. 1 is shown in FIG. 3 with a modified bearing 34. The bearing 34 is typically constructed from a material, such as polyethylene, having a low coefficient of friction to facilitate the articulation of the condyles 24, 28. Included within bearing 34 is a grounding plane 76. The grounding plane 76 is constructed from a biocompatible alloy, such as an alloy of titanium. Because the bearing material surrounding the grounding plane is non-conductive, there is no electrical connection between the stem 30 of the tibial component 14 and the grounding plane formed within the bearing 34. By electrically coupling the wireless communication module 38 to one end of the tibial component, the length of the tibial component up to the non-conductive bearing 34 operates as a monopole antenna for a frequency having a quarter-wavelength that is approximately the length of the tibial stem 30. The electromagnetic field emitted by the tibial component when excited by the wireless communication module 38 is also reflected by the grounding plane 76. The total image of the emitted and reflected field corresponds to the emitted field of a dipole antenna for a frequency having a half-wavelength in body tissue that is approximately twice the length of the tibial component.

Methods operating in accordance with the principles of the present invention may also be described with reference to FIGS. 1 and 3. One method includes electrically coupling a wireless communication module to an implant component having a metal surface and operating the implant component as an antenna for wireless communication between the wireless communication module and a data communication device external to a patient in which the implant component is implanted. The wireless communication may include receiving sensor data from a sensor, modulating a carrier wave with the received sensor data, and radiating the modulated carrier wave from the implant component acting as an antenna. The wireless communication may also include receiving a modulated carrier wave from the implant component operating as an antenna and demodulating the modulated carrier wave to obtain a data signal from the external data communication device.

In the method of the present invention, the coupling of the wireless communication module to the artificial implant may occur at a point where the length of the artificial implant that operates as an antenna is an integral number of half-wavelengths of the carrier wave. As shown in FIG. 1, this coupling may occur at a point that enables the artificial implant component to operate as a dipole antenna. This point may be located approximately at the mid-point of the artificial implant's length so the distance from the point of coupling to each end of the implant component is approximately one quarter of the wavelength of the carrier wave. As shown in FIG. 3, this coupling may occur at a point that enables the implant component to operate as a monopole antenna. In this case, the method also includes orienting a grounding plane in proximity to the implant component acting as an antenna so that the total image of the emitted and reflected fields corresponds to the emitted field of a dipole antenna. The monopole antenna configuration may be accomplished by coupling the wireless communication module to one end of an artificial implant having a length of approximately one quarter of the carrier signal wavelength. The ground plane may be positioned so it reflects the emitted field and the total emitted and reflected field configuration resembles that of a dipole antenna.

The method of the present invention also contemplates constructing an implant component for radiating carrier waves for particular communication standards. The implant component may be provided with a grounding plane so the implant component may be configured as a monopole antenna to implement a particular wireless communication standard carrier wave or it may be sized so the wireless communication module may be coupled to it to operate as a dipole antenna for a particular carrier wave.

The method of the present invention may be used to configure a tibial component for wireless communication with an external data communication device as shown in FIGS. 1-3. However, one of ordinary skill within the art would appreciate how the principles of the present invention may be applied to other orthopaedic implant components so that sensors located in proximity to a reconstructed joint or fractured bone may generate data and that data may be wirelessly communicated through an implant component to an external device. Data from such sensors may be used to modulate a carrier frequency that is coupled to an implant component and radiated to an external data communication device. The external communication device demodulates the received signal to obtain the sensor data for collection and/or processing.

While the present invention has been illustrated by the description of examples of processes and system components, and while the various processes and components have been described in considerable detail, applicant does not intend to restrict or in any way limit the scope of the appended claims to such detail. Additional advantages and modifications will also readily appear to those skilled in the art. Therefore, the invention in its broadest aspects is not limited to the specific details, implementations, or illustrative examples shown and described. Accordingly, departures may be made from such details without departing from the spirit or scope of applicant's general inventive concept.

What is claimed is:

1. A data communication system for wirelessly communicating data from within a human body to a data communication device external to the body, comprising:
    an orthopedic prosthetic implant component having a metal surface, the orthopedic prosthetic implant component being configured to replace bone tissue in a person; and
    a wireless communication module electrically coupled to the metal surface of the orthopedic prosthetic implant component so a carrier wave excites a length of the orthopedic prosthetic implant component metal surface to operate the length of the orthopedic prosthetic implant component as an antenna;
    wherein the wireless communication module is a module that excites the length of the orthopedic prosthetic implant component with a carrier wave that has been modulated with sensor data to operate the length of the implant component as antenna.

2. The system of claim 1 wherein the wireless communication module is a module for receiving a carrier wave that has been modulated with data from the length of the implant component being operated as an antenna.

3. The system of claim 1 wherein the wireless communication module is a transceiver for both transmitting and receiving carrier waves that have been modulated with data signals through the length of the implant component operated as an antenna.

4. The system of claim 1 wherein the wireless communication module is electrically coupled to the metal surface of the implant component at a point where the length of the implant component that operates as an antenna is an integral number of half-wavelengths for a carrier wave used for communication through the metal surface of the implant component operating as an antenna.

5. The system of claim 4 wherein the wireless communication module is electrically coupled to the length of the orthopedic prosthetic implant component that operates as an antenna at approximately its midpoint so that the length of the implant component that operates as an antenna operates as a dipole antenna.

6. The system of claim 4 wherein the wireless communication module is electrically coupled to the metal surface of the implant component at one end of the implant component to operate the length of the implant component as a monopole antenna emitting an electromagnetic field, and the system further comprising:
    a ground plane positioned to reflect the electromagnetic field emitted from the length of the metal surface of the implant component operating as an antenna so the reflected and emitted field of the implant component length operating as an antenna resembles an electromagnetic field emitted from a dipole antenna having a length approximately one half-wavelength of the carrier signal.

7. The system of claim 6 further comprising:
    a polyethylene insert having a ground plane within the insert and the polyethylene insert is incorporated in the implant component being operated as an antenna by the wireless communication module.

8. The system of claim 6 further comprising:
    a polyethylene insert having a ground plane within the insert and the polyethylene insert is incorporated in another orthopedic prosthetic implant component being used to reconstruct the bone tissue being replaced with the implant component operating as an antenna.

9. The system of claim 1, wherein the carrier wave that excites the length of the implant component operating as an antenna has a frequency of about 2.4 GHz.

10. A data communication system for wirelessly communicating data from a reconstructed knee comprising:
a tibial component having a metal surface, the tibial component being used to replace bone tissue in a person;
a wireless communication module that is electrically coupled to the metal surface of the tibial component; and
a sensor located proximate to the tibial component to sense a parameter near the tibial component, the sensor being coupled by a wire to the wireless communication module so that a signal generated by the sensor is provided over the wire to the wireless communication module and the wireless communication module uses the signal received from the sensor to modulate a carrier wave that is applied to the metal surface of the tibial component by the wireless communication module to excite the metal surface of the tibial component and operate the tibial component as an antenna for radiation of the modulated carrier wave to an external data device.

11. The system of claim 10, the metal surface of the tibial component is coupled to the wireless communication module at a point along the metal surface that enables the wireless communication module to operate the tibial component as a dipole antenna.

12. The system of claim 10, the metal surface of the tibial component is coupled to the wireless communication module at a point along the metal surface that enables the wireless communication module to operate the tibial component as a monopole antenna; and the system further includes:
a ground plane positioned to reflect an electromagnetic field emitted by the metal surface of the tibial component so the emitted and reflected field of the tibial component operating as a monopole antenna resembles a field produced by a dipole antenna excited by a carrier wave having a frequency that is the same frequency as the carrier wave that excites the metal surface of the tibial component operating as a monopole antenna.

13. A method for wirelessly communicating data from within a human body to a device external to the human body, comprising:
electrically coupling a wireless communication module to an orthopedic prosthetic implant component having a metal surface, the orthopedic prosthetic implant component being used to replace bone tissue in a patient; and
operating the orthopedic prosthetic implant component as an antenna for wireless communication between the wireless communication module and a data communication device external to a patient in which the implant component has been used to replace bone tissue.

14. The method of claim 13 further comprising:
exciting the metal surface of the orthopedic prosthetic implant component with a modulated carrier wave to operate the orthopedic prosthetic implant component as an antenna.

15. The method of claim 13 further comprising:
receiving a modulated carrier wave from the metal surface of the implant component operating as an antenna.

16. The method of claim 14 further comprising:
modulating the carrier wave used to excite the metal surface of the implant component with sensor data received from a sensor coupled to the wireless communication module.

17. The method of claim 15 further comprising:
demodulating the modulated carrier wave received from the metal surface of the implant component to obtain a data signal from the external data communication device.

18. The method of claim 13, the coupling of the wireless communication module to the implant component further comprising:
coupling the wireless communication module to the metal surface of the implant component at a point on the metal surface of the implant component to provide a length of the metal surface that is an integral number of half-wavelengths of the carrier wave.

19. The method of claim 13, the coupling of the wireless communication module to the implant component further comprising:
coupling the wireless communication module to the metal surface of the implant component at a point that enables the implant component to operate as a dipole antenna for a carrier wave frequency.

20. The method of claim 13, the coupling of the wireless communication module to the implant component further comprising:
coupling the wireless communication module to the metal surface of the implant component at a point that enables the implant component to operate as a monopole antenna; and the method also includes:
positioning a ground plane to reflect an electromagnetic field emitted by the metal surface of the implant component so that the reflected and emitted field of the monopole antenna corresponds to one generated by a dipole antenna.

21. The method of claim 20 further comprising:
incorporating an polyethylene insert having the ground plane within the polyethylene insert in the implant component that is operating as an antenna.

22. The method of claim 20 further comprising:
incorporating an polyethylene insert having the ground plane within the polyethylene insert in an implant component that is being used to replace the bone tissue, the implant component incorporating the polyethylene insert is not operated as an antenna to radiate a modulated carrier wave.

23. The method of claim 13 further comprising:
variably tuning the external data communication device until a response signal is received from the wireless communication module through a length of the metal surface of the implant component operating as an antenna; and
determining the length of the implant component operating as an antenna from the frequency of the response signal.

24. A method for wirelessly communicating data from a reconstructed knee, comprising:
electrically coupling a wireless communication module to a metal surface of a tibial component that is used to replace bone tissue in a person for wireless communication with an external data communication device;
coupling a sensor to the wireless communication module;
modulating a carrier wave with data received from the sensor coupled to the wireless communication module; and
exciting the metal surface of the tibial component with the modulated carrier wave to radiate the modulated carrier wave from the metal surface of the tibial component operating as an antenna and replacing bone tissue in a person.

25. The method of claim 24 further comprising:
demodulating the modulated carrier wave to obtain the data used to modulate the carrier frequency.

26. The method of claim 24, the metal surface of the tibial component being coupled to the wireless communication module at a point that enables the tibial component to be operated as a monopole antenna; and the method further includes:
positioning a ground plane to reflect an electromagnetic field emitted by the metal surface of the tibial component operating as a monopole antenna so that the emitted field and reflected field corresponds to that produced by a dipole antenna for a carrier wave having the same frequency as the carrier wave modulated with the sensor data.

27. The method of claim 26, further comprising:
incorporating the ground plane within a polyethylene insert on the tibial component to reflect the electromagnetic field emitted by the metal surface of the tibial component.

28. The method of claim 24 further comprising:
variably tuning an external data communication device so the wireless communication module provides a response signal to the external device through a length of the metal surface of the tibial component operating as an antenna; and
determining the length of the metal surface of the tibial component that is being operated as an antenna from the frequency on which the response signal was received.

* * * * *